(12) United States Patent
Narita (10) Patent No.: US 10,039,931 B2
(45) Date of Patent: Aug. 7, 2018

(54) ACCELERATING METHOD, OPTOMEDICAL DEVICE, AND OPTOMEDICAL SYSTEM

(71) Applicant: Terumo Kabushiki Kaisha, Tokyo (JP)

(72) Inventor: Makoto Narita, Hadano (JP)

(73) Assignee: TERUMO KABUSHIKI KAISHA, Tokyo (JP)

( * ) Notice: Subject to any disclaimer, the term of this patent is extended or adjusted under 35 U.S.C. 154(b) by 410 days.

(21) Appl. No.: 14/539,163

(22) Filed: Nov. 12, 2014

(65) Prior Publication Data
US 2015/0142086 A1 May 21, 2015

(30) Foreign Application Priority Data

Nov. 15, 2013 (JP) .................................. 2013-237208

(51) Int. Cl.
*A61N 5/06* (2006.01)

(52) U.S. Cl.
CPC ......... *A61N 5/0601* (2013.01); *A61N 5/0622* (2013.01); *A61N 2005/0602* (2013.01); *A61N 2005/0627* (2013.01); *A61N 2005/0661* (2013.01); *A61N 2005/0663* (2013.01)

(58) Field of Classification Search
CPC ............................ A61N 5/0622; A61N 5/0601
USPC ......................................................... 607/88
See application file for complete search history.

(56) References Cited

U.S. PATENT DOCUMENTS

| 8,715,327 B1* | 5/2014 | Lovett ................. A61N 5/0622 607/88 |
| 2003/0083698 A1* | 5/2003 | Whitehurst ....... A61M 5/14276 607/3 |
| 2013/0138182 A1* | 5/2013 | Nissila ................ A61N 5/0618 607/88 |
| 2014/0066949 A1* | 3/2014 | Eskuri ................. A61N 1/0529 606/127 |

FOREIGN PATENT DOCUMENTS

| JP | 2006-525039 A | 11/2006 |
| WO | WO-2004/096364 A1 | 11/2004 |

OTHER PUBLICATIONS

Document submitted to Japanese Patent Office dated Dec. 9, 2013 with partial English translation providing brief explanation.

* cited by examiner

*Primary Examiner* — Amanda Hulbert
*Assistant Examiner* — Philip C Edwards
(74) *Attorney, Agent, or Firm* — Foley & Lardner LLP (57) ABSTRACT

A method for accelerating the release of neurotransmitters includes a step of radiating light from within a cerebral blood vessel to accelerate the release of the neurotransmitters. An optomedical device includes a main body configured to be introduced into a cerebral blood vessel; a light emitting unit arranged on the main body, the light emitting unit configured to radiate light to accelerate the release of neurotransmitters; and a control unit configured to control a light emitting action of the light emitting unit.

16 Claims, 9 Drawing Sheets

ACCELERATING METHOD, OPTOMEDICAL DEVICE, AND OPTOMEDICAL SYSTEM

CROSS-REFERENCE TO RELATED APPLICATIONS

This application claims priority to Japanese Patent Application No. 2013-237208, filed on Nov. 15, 2013, which is hereby incorporated by reference in its entirety.

BACKGROUND

Technical Field

The present disclosure relates to a method for accelerating the release of neurotransmitters, an optomedical device, and an optomedical system.

Background Art

It is a well-known fact that a variety of neurotransmitters secreted in the human brain greatly affect the human's mental state and physiological state. It is believed, for example, that the amount of secretion of neurotransmitters is closely related with the onset of such mental diseases as depression, panic disorder, and schizophrenia. Among neurotransmitters most influential on the mental state are those of monoamine type such as dopamine, serotonin, and noradrenaline.

For example, depression is caused by a decrease in secretion of dopamine and ADHD (attention-deficit-hyperactivity-disorder) is caused by an unsmooth transfer of dopamine resulting from anomaly in the neurotransmission pathway. Moreover, mental disease and sleep disorder are caused by the lack of secretion of serotonin.

There has been proposed in JP-T-2006-525039 a medical device which is intended to prevent the onset of sleep disorder by controlling the secretion of serotonin. Serotonin is secreted when the photoreceptor in the retina receives blue light. And the secretion of serotonin accelerates the secretion of melatonin to adjust the human sleep cycle. This knowledge is the base of the medical device disclosed in JP-T-2006-525039. In other words, the medical device accelerates the secretion of serotonin by directing light to the retina from the outside of the living body.

Unfortunately, the above-mentioned medical device has the disadvantage of needing comparatively intensive light beams directed to the retina for the secretion of neurotransmitters such as serotonin. This would cause an adverse effect on the human body.

SUMMARY OF INVENTION

In light of the foregoing, certain embodiments of the present invention are intended to provide a method for adequately accelerating the release of neurotransmitters, an optomedical device, and an optomedical system which will be applied to the human body with a minimum of burden thereon.

According to one embodiment, an accelerating method includes a step of photoirradiation to accelerate the release of neurotransmitters, the step being accomplished by radiating light within a cerebral blood vessel. This step stimulates the photoreceptor existing in the brain, thereby adequately accelerating the release of neurotransmitters. The acceleration in this manner imposes a less amount of burden on the body than that by irradiating the retina with light.

In one aspect, the step of photoirradiation is accomplished by directing the light radiated from within the cerebral blood vessel to the pineal body. Light radiation in this manner efficiently accelerates the release of neurotransmitters.

In one aspect, the cerebral blood vessel is the posterior cerebral artery and/or a side branch thereof. The radiation of light in this manner ensures the arrival of light to the pineal body, thereby accelerating the efficient release of neurotransmitters.

In one aspect, the side branch of the posterior cerebral artery is the medial posterior choroidal artery. The radiation of light in this manner ensures the arrival of light to the pineal body, thereby accelerating the more efficient release of neurotransmitters.

In one aspect, the step of photoirradiation includes irradiation with ultraviolet light. The radiation of ultraviolet light accelerates the release of dopamine as one of neurotransmitters. This helps improve and remedy various diseases resulting from the deficient secretion of dopamine or the anomalous transmission of dopamine through the neurotransmission pathway.

In one aspect, the step of photoirradiation includes irradiation with blue light. The radiation of blue light accelerates the release of serotonin as one of neurotransmitters. This helps improve and remedy various diseases resulting from the deficient secretion of serotonin.

In one aspect, the accelerating method further includes a step of introducing into the cerebral blood vessel an optomedical device having a light emitting unit to radiate the light. This optomedical device radiates light through the wall of the blood vessel, thereby accelerating the secretion of neurotransmitters.

In one aspect the optomedical device includes a main body of stent type capable of indwelling in the cerebral blood vessel, and the light emitting unit is arranged on the outer surface of the main body. The indwelling optomedical device remains in the blood vessel without hindering the blood flow, thereby adequately preventing thrombosis.

In one embodiment, an optomedical device includes a main body to be introduced into the cerebral blood vessel, a light emitting unit arranged on the main body which radiates light to accelerate the release of neurotransmitters, and a control unit to control the action of the light emitting unit. This device is capable of accelerating the release of neurotransmitters by irradiating with light from the inside of the blood vessel, thereby stimulating the photoreceptor existing in the brain. The therapy in this way reduces burden on the human body.

In one aspect, the main body is composed of a barrel part and openings formed at both ends thereof, in order to allow the main body to be deformed and expanded in the cerebral blood vessel. This structure allows its easy operation for indwelling and its stable indwelling over a long period of time.

In one aspect, the light emitting unit is arranged on the outer surface of the main body. This structure prevents the light emitting unit from hindering the blood flow, thereby avoiding possible thrombosis due to the indwelling optomedical device.

In one aspect, the main body is formed in a cylindrical shape. This structure permits the optomedical device to indwell in such a state that the main body remains in contact with the inner wall of the cerebral blood vessel in its lengthwise direction over a prescribed range. The result is stable indwelling for a long period of time.

In one aspect, the main body is formed in a ring shape. Because of this structure, the optomedical device permits blood to flow smoothly through the cerebral blood vessel after its indwelling.

In one aspect, the light emitting unit is one which radiates ultraviolet light and/or blue light. Radiation of ultraviolet light and/or blue light accelerates the release of neurotransmitters such as dopamine and serotonin.

In one aspect, the control unit is so constructed as to activate and deactivate the light emitting action of the light emitting unit in response to a preset hour and/or a preset time interval. Control in this manner accelerates the release of neurotransmitters according to adequate timing.

In one embodiment, an optomedical system includes an optomedical device, which includes a main body to be introduced into the cerebral blood vessel, a light emitting unit arranged on the main body which radiates light to accelerate the release of neurotransmitters, and a control unit to control the action of the light emitting unit in which the main body is composed of a barrel part and openings formed at both ends thereof, in order to allow the main body to be deformed and expanded in the cerebral blood vessel, and an operating device to control, through control signals transmitted from the outside of a living body, the action of the light emitting unit of the optomedical device which has been introduced into a living body, wherein the control unit of the optomedical device is so constructed as to activate and deactivate the light emitting action of the light emitting unit in response to control signals transmitted from the operating device.

In one aspect, the control device has a detecting unit to detect the physiological state of the living body so that it transmits the control signals in response to the result detected by the detecting unit. Control in this manner accelerates or suspends the release of neurotransmitters according to adequate timing.

In one aspect, the detecting unit detects the physiological state of the living body by observations on the movement of the eyes of the living body. Thus the optomedical system allows accurate detection of change in physiological state based on difference in eye movement.

In one aspect, the detecting unit acquires sampling values from the amount of drift of a drift eyeball movement which an eyeball of the eye undergoes when the living body views a certain object, and the operating device further possesses a memory unit to store a first and a second threshold value which serve as indexes to show the physiological state in response to the amount of drift of the drift eyeball movement and also possesses a determination unit to determine whether or not the sampling values acquired by the detecting unit is between the first threshold value and the second threshold value, and the operating device transmits control signals to activate the light emitting action if the determination unit determines that the sampling value is within the first threshold value and also transmits control signals to deactivate the light emitting action if the determination unit determines that the sampling value is within the second threshold value. Thus, this optomedical system clearly discriminates the physiological state of the living body which may be classified by the eyeball movement.

In one aspect, the operating device transmits control signals to deactivate the light emitting action if the detecting unit detects that the living body is in a sleeping state. This function simplifies efforts to operate the optomedical device indwelling in the cerebral blood vessel.

In one aspect, the operating device repeats, over a prescribed time period, the detection of the physiological state by the detecting unit and the transmission of control signals based on the result of detection of the physiological state. Therefore, this system activates and deactivates the light emitting action at any time in response to the physiological state of the subject while the optomedical device is indwelling in the cerebral blood vessel.

In one aspect, the operating device includes a unit resembling an eyeglass frame mountable on the ears of the living body. This structure permits the operating device to be reduced in size and the optomedical system to be used inconspicuously.

BRIEF DESCRIPTION OF THE DRAWINGS

FIGS. 1A, 1B, and 1C are diagrams illustrating an optomedical system according to a first embodiment.

FIGS. 2A and 2B are diagrams illustrating the structure of the human brain.

FIGS. 3A and 3B are diagrams illustrating an optomedical device being used in a typical way.

DETAILED DESCRIPTION

Embodiments of the present invention will be described below with reference to the accompanying drawings. Incidentally, the drawings are made in an exaggerated ratio, instead of a real ratio, for clear illustration.

The First Embodiment

Figure 1A:
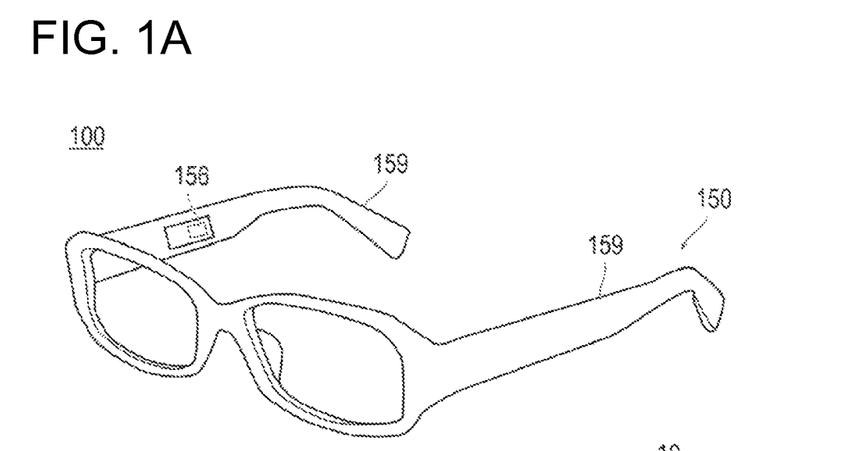
FIG. 1A is a schematic diagram of an operating device.
Figure 1B:
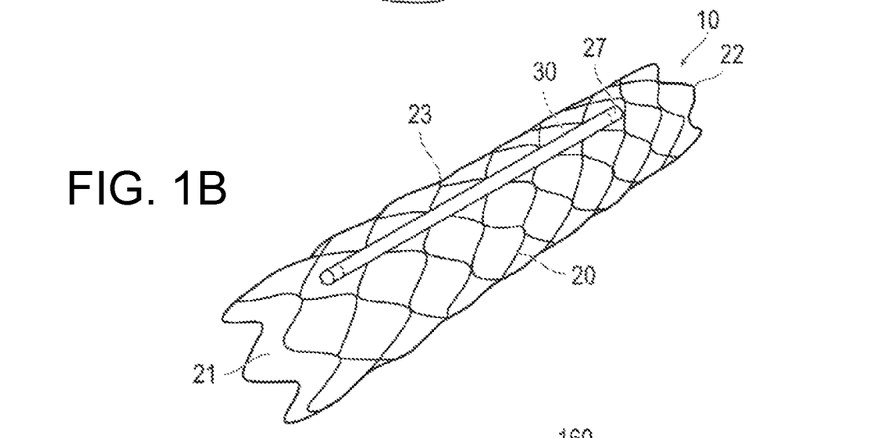
FIG. 1B is a schematic diagram of an optomedical device.
Figure 1C:
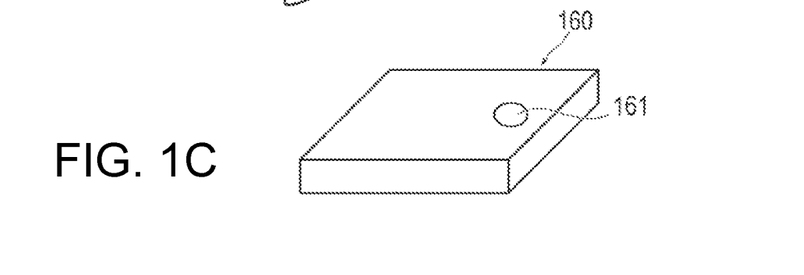
FIG. 1C is a schematic diagram of a current supply device.
Figure 2A:
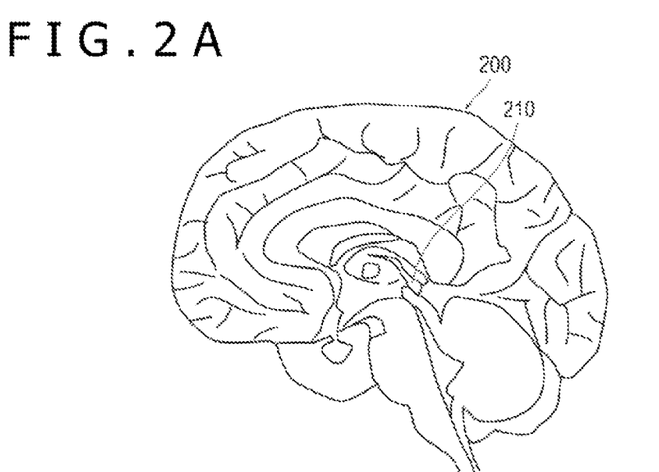
FIG. 2A is a schematic sagittal sectional view of the brain.
Figure 2B:
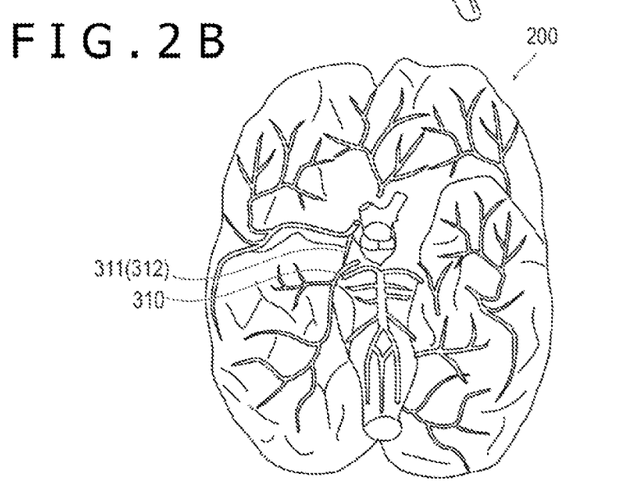
FIG. 2B is a schematic sectional diagram showing the entire brain as viewed from the cerebral base.
Figure 3A:
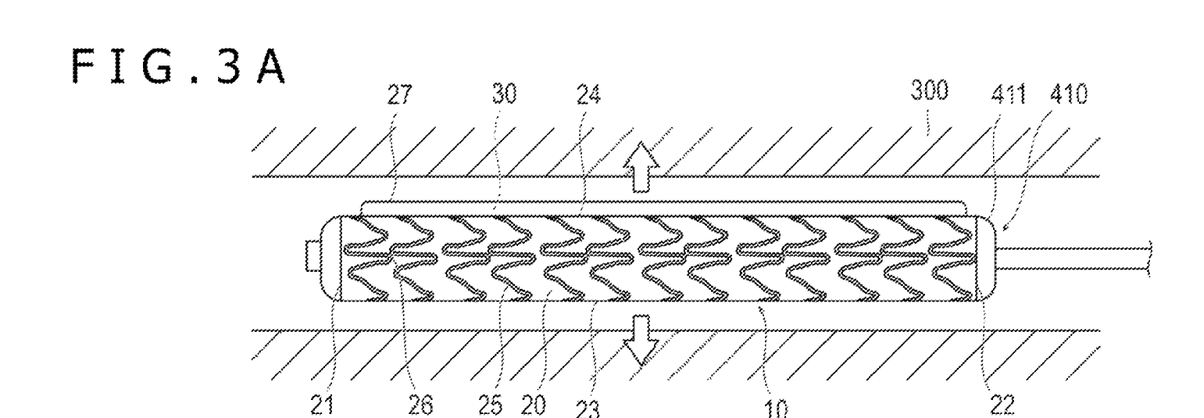
FIG. 3A is a schematic longitudinal sectional view illustrating how to introduce the optomedical device into the cerebral blood vessel.
Figure 3B:
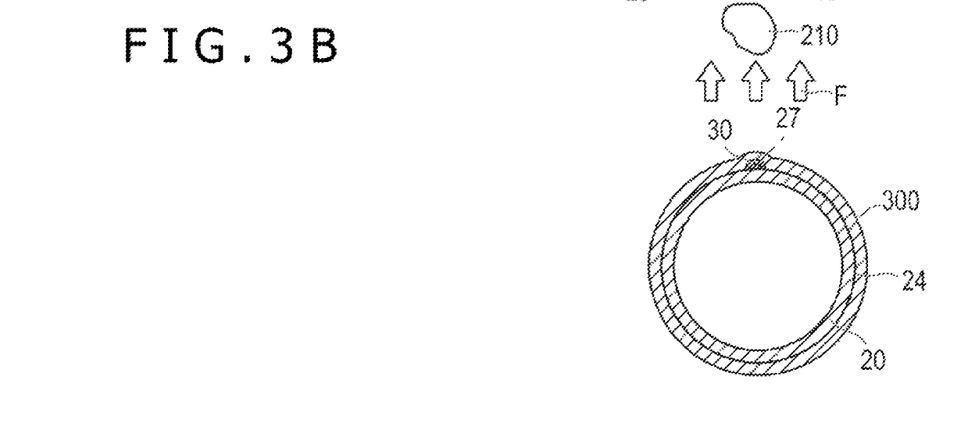
FIG. 3B is a schematic cross sectional view showing how the optomedical device radiates light toward the pineal body.
Figure 4:
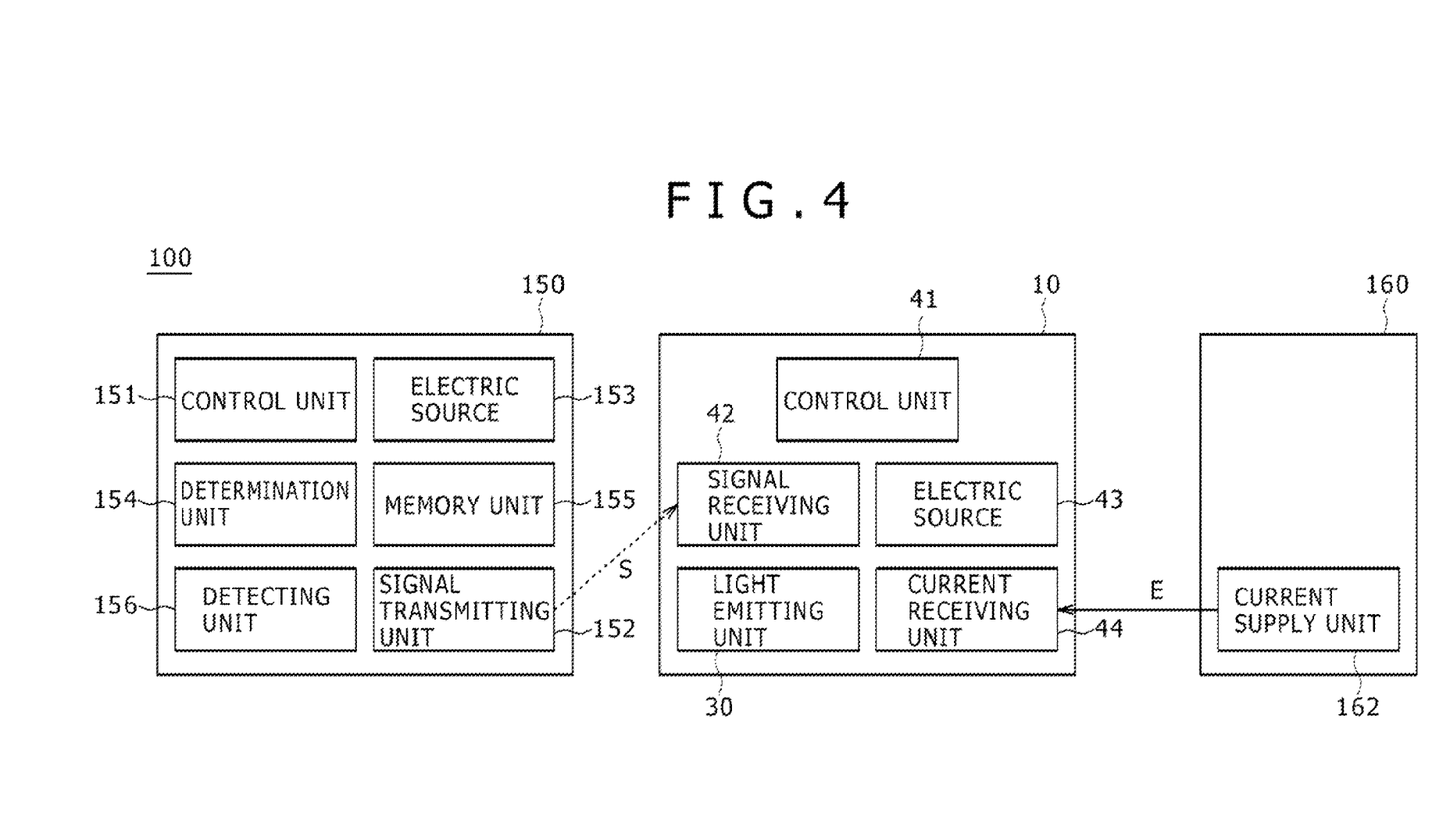
FIG. 4 is a simplified block diagram showing the entire configuration of the optomedical system.
Figure 5:
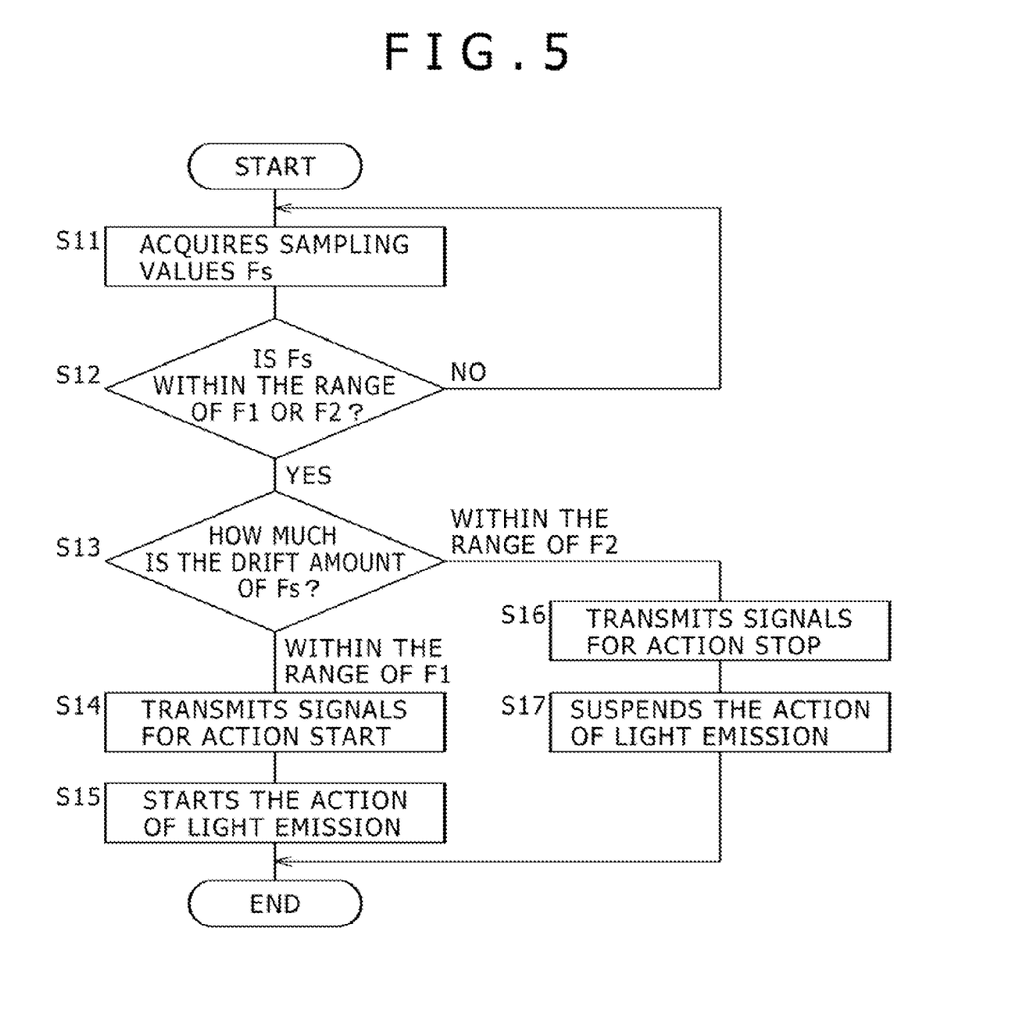
FIG. 5 is a flowchart showing how the optomedical system controls its action.
Figure 6:
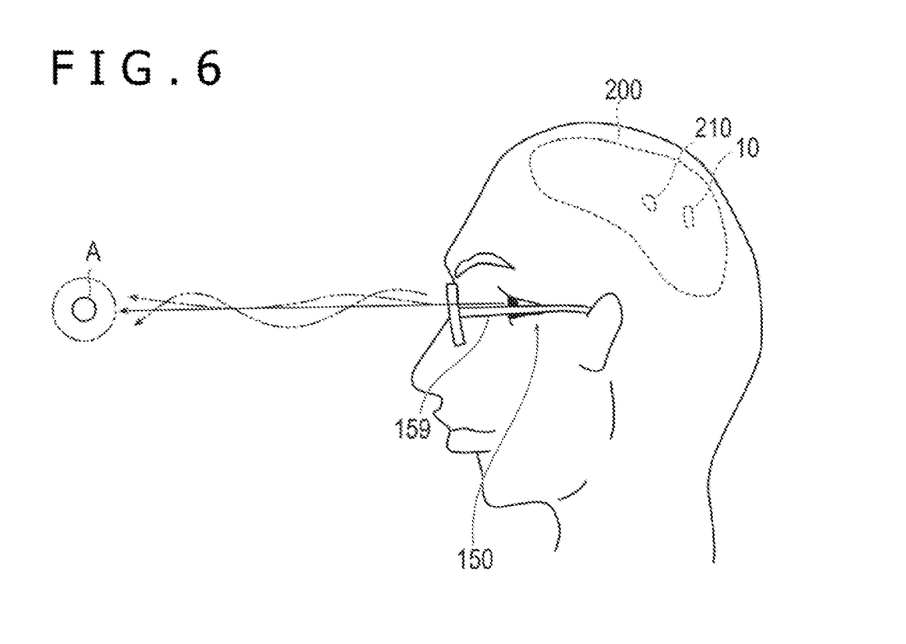
FIG. 6 is a diagram illustrating how a detecting unit of the optomedical system functions.

FIGS. 1A-1C are diagrams illustrating the optomedical device and optomedical system pertaining to the first embodiment. FIGS. 2A and 2B are diagrams illustrating the structure of the human brain to which the optomedical device is applied. FIGS. 3A and 3B are diagrams illustrating the optomedical device and optomedical system being used in a typical way. FIGS. 4 to 6 are diagrams illustrating the configuration and function of the optomedical device and optomedical system.

As shown in FIG. 1B, FIGS. 3A and 3B, and FIG. 4, an optomedical device 10 includes a main body 20 to be inserted into a cerebral blood vessel 300, a light emitting unit 30 attached to the main body 20 which radiates light to accelerate the release of neurotransmitters, and a control unit 41 which controls the action of the light emitting unit 30.

The optomedical device 10 is intended to radiate light within the cerebral blood vessel 300 of a subject (living body), thereby accelerating the secretion (release) of neurotransmitters. According to the embodiment shown in FIGS. 1A-1C, an optomedical system 100 includes the optomedical device 10 and an operating device 150 intended for operation of the optomedical device 10. In addition, the optomedical system 100 is provided with a current supply device 160 to energize the optomedical device 10.

In what follows, FIG. 2A will be referenced to explain the structure of the human brain and the mechanism by which the optomedical device accelerates the release of neurotransmitters.

The human retina has cells which, upon reception of light from outside, transmit signals to stimulate the secretion of dopamine or serotonin as one kind of neurotransmitters. It is known that serotonin is produced from tryptophan (which is one kind of ingested essential amino acid) and this process is accelerated when the retina receives natural light. The secreted serotonin turns into melatonin after a certain period of time and the resulting melatonin is secreted from a pineal body 210 in the brain. Eventually, melatonin induces sleep.

Moreover, the results of recent researches show that the pineal body 210 contains cells similar to those in the retina. In other words, it has been found that the pineal body 210 functions in the same way as the retina, that is, upon reception of light, it transmits signals to accelerate the secretion of dopamine or serotonin.

In fact, ultraviolet light emitted from the optomedical device 10 and directed to the pineal body 210 stimulates the light receiving molecules existing in the pineal body 210, thereby causing dopamine to be secreted from the nerve terminal. The increased secretion of dopamine, in turn, increases the secretion of noradrenaline, thereby activating the brain and improving the symptom of ADHD and the like. Moreover, blue light emitted from the optomedical device 10 and directed to the pineal body 210 stimulates the light receiving molecules existing in the pineal body 210, thereby causing serotonin to be secreted from the nerve terminal. The increased secretion of serotonin, in turn, increases the secretion of melatonin, thereby improving the symptom of mental disorder (such as depression) and sleep disorder.

The following describes, with reference to FIG. 2B, the brain blood vessel into which the optomedical device is introduced.

To apply the method for accelerating the secretion of neurotransmitters with the help of the optomedical device 10, it is necessary to introduce the optomedical device 10 into the prescribed cerebral blood vessel 300. Since a human brain 200 is covered with the skull, the brain surface is hardly irradiated with light (particularly ultraviolet light) directed thereto from the outside of the human body. This problem is addressed by irradiating the brain 200 with light from the inside of the skull. In this way it is possible to effectively stimulate the light receiving molecules without reduction in the amount of light irradiated.

The optomedical device 10 may be introduced into any one of a posterior cerebral artery 310 (which is the cerebral blood vessel 300), a side branch 311 of the posterior cerebral artery 310, and a medial posterior choroidal artery 312 (which is one of the side branches 311 of the posterior cerebral artery 310). These arteries are near the pineal body 210 existing within the brain 200. As mentioned above, the pineal body 210 has the dopamine receptor and serotonin receptor. Therefore, radiation of light from within any of the arteries efficiently accelerates the secretion of dopamine and serotonin.

The following describes the structure of the optomedical device and optomedical system.

As shown in FIG. 1B and FIGS. 3A and 3B, the optomedical device 10 includes the main body 20, which has a first opening 21 (formed on one end), a second opening 22 (formed on the other end), and a barrel 23 connecting to the first and second openings 21 and 22. The main body 20 is so constructed as to deform and expand in the cerebral blood vessel 300. The one end and the other end of the main body 20 orient in the axial direction in which the main body 20 extends.

The barrel 23 has a hollow space which permits a fluid to pass through it. The light emitting unit 30 may be arranged on an outer surface 24 of the main body 20, for example.

The main body 20 is formed in a cylindrical shape, so that it expands outwards in its radial direction. In other words, the main body 20 is constructed such that it deforms and expands toward the inner wall of the blood vessel after it has been introduced into the cerebral blood vessel 300.

The main body 20 of the optomedical device 10 includes the stent which is known in the field of medicine. The stent consists of a plurality of rings 25 (each formed from a wavy strut) which are arranged side by side. The rings 25 are connected with one another by a link 26. The stent is of the balloon expandable type. Therefore, a balloon catheter 410 is employed for the optomedical device 10 to be introduced for indwelling in the cerebral blood vessel 300.

The main body 20 of the optomedical device 10 is not specifically restricted in length, inner diameter, and outer diameter so long as it is capable of introduction into the cerebral blood vessel 300. For example, the length may range from 5 to 50 mm, the inner diameter may range from 0.5 to 5 mm, and the outer diameter may range from 1 to 6 mm.

The main body 20 may be formed from any known material which is used for the stent of balloon expandable type. Examples of the material include iron, titanium, aluminum, tin, tantalum (or alloy thereof), platinum (or alloy thereof), gold (or alloy thereof), titanium alloy, nickel-titanium alloy, cobalt-base alloy, cobalt-chromium alloy, stainless steel, zinc-tungsten alloy, and niobium alloy.

The stent constituting the main body 20 may also be that of self-expandable type. The stent of self-expandable type may be delivered into the cerebral blood vessel 300 in any known way applied to the catheter system. It may also be formed from nickel-titanium alloy.

The light emitting unit 30 radiates light having an adequate wavelength that can be controlled by the control unit 41 attached to the optomedical device 10. The wavelength of light can be varied according to the neurotransmitter that needs accelerated secretion. According to this embodiment, the light emitting unit 30 is capable of radiating ultraviolet light (200 to 344 nm in wavelength) and blue light (344 to 420 nm in wavelength). These two kinds of light are emitted from two kinds of light-emitting diodes.

The light emitting unit 30 should be so constructed as to radiate light (which accelerates the secretion of neurotransmitters) within the cerebral blood vessel 300. So long as this requirement is met, it is not specifically restricted in the wavelength, amount, and mode of light to be radiated. For example, it may be so constructed as to radiate directional light straight, radiate light scattering in many directions, or radiate light in controllable directions.

The light emitting unit 30 is encased in an enclosure 27 attached to the main body 20. The enclosure 27 may be formed from any transparent or translucent material that passes the light emitted from the light emitting unit 30. It may also be formed from any known biocompatible material in consideration of the fact that the optomedical device 10 is introduced into a living body.

The enclosure 27 may be attached to the main body 20 in any known way, such as adhesion, fusion bonding, and solvent welding, which should be selected from the standpoint of the material from which the main body 20 and the enclosure 27 are formed. The enclosure 27 is not specifically restricted in shape and dimensions so long as it is constructed such that it can encase therein the light emitting unit 30.

As shown in FIG. 3A, the light emitting unit 30 may be arranged in such a way that it extends up to a prescribed length in the direction in which the main body 20 extends. Arrangement in this manner permits light radiation in a comparatively large range, which leads to the efficient release of neurotransmitters.

FIG. 4 is a block diagram which schematically illustrates the configuration of the optomedical system.

The optomedical device 10 includes the light emitting unit 30, the control unit 41, a signal receiving unit 42, an electric source 43, and the current receiving unit 44.

The control unit 41 generally controls the action of the optomedical device 10. The signal receiving unit 42 receives control signals transmitted from the operating device 150. The control unit 41 activates and deactivates the light emitting action of the light emitting unit 30 in response to the received control signals. An arrow S in FIG. 4 represents the control signals transmitted and received.

The control unit 41 may be any known central processing unit (CPU) as its major constituent. It may additionally include a timer to control the timing for light emission at a prescribed hour and/or a prescribed interval.

The signal receiving unit 42 may be based on hardware for wireless communications included in the control unit 41.

The electric source 43 turns on and off the light emitting unit 30.

The current receiving unit 44 receives electric power from the current supply deice 160.

The control unit 41, signal receiving unit 42, electric source 43, and current receiving unit 44 may all be encased in the enclosure 27 with the light emitting unit 30.

The current supply device 160 and the current receiving unit 44 constitute a current supply system that supplies the optomedical device 10 with current wirelessly. The current supply system installed in the optomedical system 100 allows current to be supplied externally to the optomedical device 10 introduced into the cerebral blood vessel 300. Incidentally, an arrow E in FIG. 4 represents electric power supplied to the current receiving unit 44.

The current supply device 160 may be equipped with a current supply unit 162 of wireless type which is based on electromagnetic induction, radio transmission, resonance, etc. The electromagnetic induction for current supply, however, should desirably be avoided because it causes heat generation in the main body 20 of the optomedical device 10.

The current supply by the current supply device 160 is started and suspended as a power switch 161 in the current supply device 160 is turned on and off (shown in FIG. 1C).

The following describes the operating device 150 with reference to FIGS. 1 and 4.

The operating device 150 functions as a controller to operate the light emitting unit 30 from the outside of the living body.

The operating device 150 has a detecting unit 156 to detect the physiological state of the subject. As shown in FIG. 4, the operating device 150 transmits control signals for the optomedical device 10 to activate and deactivate the light emitting action in response to the results of detection by the detecting unit 156. For the optomedical device 10 to work properly, it should be placed in the subject's cerebral blood vessel 300 and the operating device 150 should be placed outside the living body.

The detecting unit 156 is so constructed as to detect the physiological state of the subject by observation of the subject's eye movement. According to this embodiment, the detecting unit 156 observes the drift eyeball movement which the eyeball experiences when the subject stares an object, and it acquires sampling values from the amount of drift thus observed.

The detecting unit 156 is not specifically restricted in its construction so long as it is capable of detecting the amount of drift of the drift eyeball movement. It may be any known sensor such as complementary metal-oxide semiconductor (CMOS) sensor and charge-coupled device (CCD) sensor. The operating device 150 functions as a detector to detect the physiological state (owing to the detecting unit 156 therein), and it also functions as a control device to control the action of the optomedical device 10 in response to the physiological state.

As shown in FIGS. 1 and 6, the operating device 150 may be constructed in the form resembling the frame 159 of an eyeglass so that it can be worn on the subject's ears. The operating device 150 resembling the frame 159 in its form is small in size and smart in appearance. The frame 159 may be provided with lenses so that it functions as an eyeglass.

The detecting unit 156 may be placed at any position in the operating device 150. In the case where the operating device 150 has the frame 159, the detecting unit 156 may be placed on the inside surface of the frame 159. The detecting unit 156 placed at such a position is comparatively close to the eye during use, so that it easily detects the eyeball movement and swiftly responds to the eyeball movement. Several detecting units 156 may be placed detection of physiological state.

The operating device 150 may be constructed such that it is placed at a position away from the subject's face, on one ear (instead of two ears), or on the head or face. In addition, the operating device 150 may also be provided with the operating switch to change the characters (such as wavelength, light amount, and radiation mode) of the light radiated from the optomedical device 10.

As shown in FIG. 4, the operating device 150 includes a control unit 151 to generally control the action of the operating device 150, an electric source 153 to supply current to the operating device 150, a determination unit 154 and a memory unit 155 which are necessary to execute the algorithm according to the flowchart explained later, a signal transmitting unit 152 to transmit control signals to the optomedical device 10 in response to the results produced by the determination unit 154, and the detecting unit 156.

The control unit 151 in the operating device 150 may be based on a CPU as in the case of the control unit 41 in the optomedical device 10. The signal transmitting unit 152 may be the same hardware for radio communications as installed in the control unit 151.

The control unit 151 may also function as the determination unit 154 when it executes previously installed programs. The control unit 151 also functions as the memory unit 155 which stores the threshold value to be used for determination by the determination unit 154.

The following describes the function of the determination unit.

The determination unit 154 compares a sampling value Fs (which has been acquired from the detecting unit 156) with a prescribed threshold value. The results of comparison are used for the control unit 151 to transmit control signals to the optomedical device 10. The threshold value is the one which is previously stored in the memory unit 155. This threshold value represents a first threshold value F1 and a second threshold value F2, which are indexes indicating the physiological state in response to the amount of drift of the drift eyeball movement.

The following describes, with reference to FIG. 6, the physiological sates of the human body which are classified according to the first threshold value F1 and the second threshold value F2.

When a human views an object A, the eyeball moves to capture the object A. After a continued viewing action for a certain period of time, the eyeball begins to move irregularly in a certain cycle. This movement is called flicks. The flicks cause the visual line to move around in the vicinity of the object A. This movement is called "fluctuation of visual line."

The flicks are classified into drift (or drift eyeball movement), which is a small smooth movement with low frequencies, small jumping movements, and tremor, which is a very small movement with high frequencies. The magnitude of flicks vary depending on fatigue and disorder. It is known, for example, that the magnitude of drift eyeball movement varies depending on whether the power of concentration is high or low.

As the power of concentration increases or decreases, the power spectrum (in terms of dB) of the drift eyeball movement varies especially in frequencies between 3 and 4 Hz. The power spectrum (or the amount of drift) fluctuates more when concentration is low than when concentration is high. This means that it would be possible to determine the physiological state of the subject (or determine whether the subject is in a high concentrated state or low concentrated state) by detecting the movement of the eyeball of the subject viewing the object A and then calculating the power spectrum in the frequency range from the results of detection.

According to this embodiment, the first threshold value F1 is defined as the amount of drift correlating with the power spectrum in the frequency range which is observed when the subject is in the state of low concentration, and the second threshold value F2 is defined as the amount of drift correlating with the power spectrum in the frequency range which is observed when the subject is in the state of high concentration. If the determination unit 154 determines that the sampling value Fs (which has been detected by the detecting unit 156 in the operating device 150) is within the range of the first threshold value F1, the optomedical device 10 performs the light emitting action, thereby accelerating the release of neurotransmitters from the brain. Incidentally, the first threshold value F1 and the second threshold value F2 have the upper and lower limits as indexes for determination of the physiological state of the subject.

The following describes how the operating device typically controls the action of the optomedical device.

The action control is executed according to the algorithm shown in FIG. 5.

First, the subject wears the operating device 150 and turns on its current source. In Step 11, the detecting unit 156 begins acquiring the sampling value Fs.

Next, in Step 12, the determination unit 154 determines whether or not the sampling value Fs is within the range of the first threshold value F1 or the range of the second threshold value F2.

If the determination unit 154 determines in Step 12 that the sampling value Fs is outside the range of the first threshold value F1 or the range of the second threshold value F2, the operating device 150 does not transmit control signals to the optomedical device 10. In this case, the procedure returns to Step 11 for acquisition of the sampling vale Fs.

On the other hand, if the determination unit 154 determines in Step 12 that the sampling value Fs is within the range of the first threshold value F1 or the range of the second threshold value F2, the procedure proceeds to Step 13.

In Step 13, a determination is made on whether or not the sampling value Fs is within both the range of the first threshold value F1 and the range of the second threshold value F2.

If a determination is made in Step 13 that the sampling value Fs is within the range of the first threshold value F1, the procedure proceeds to Step 14.

In Step 14, the operating device 150 transmits control signals to the optomedical device 10 for it to start the light emitting action. Upon receipt of control signals, the optomedical device 10 starts the action of radiating light from the light emitting unit 30 (Step 15). Incidentally, in the case where the light emitting device 30 has already been radiating light, signals for continued light emission are transmitted.

If a determination is made in Step 13 that the sampling value Fs is within the range of the second threshold value F2, the procedure proceeds to Step 16.

In Step 16, the operating device 150 transmits control signals to the optomedical device 10 for it to suspend the action of light radiation. Upon receipt of such control signals, the optomedical device 10 causes the light emitting unit 30 to suspend the action of light radiation (Step 17). Incidentally, in the case where the light emitting unit 30 has not yet started the action of light radiation, no control signals are transmitted and the light emitting unit 30 remains in inactive.

The following describes the process for accelerating the release of neurotransmitters. In this description, dopamine is assumed as the neurotransmitter.

First, the optomedical device 10 is introduced into any one of the cerebral blood vessels 300, which may be, for example, the posterior cerebral artery 310 selected without specific restrictions.

Introduction of the optomedical device 10 may be accomplished by using a balloon catheter 410, which is in common use in the medical field, as illustrated in FIG. 3A. The balloon catheter 410 may be that of on-the-wire type or rapid exchange type.

Before introduction of a balloon 411 into the posterior cerebral artery 310, the main body 20 of the optomedical device 10 is attached to the outer periphery of the balloon 411 of the balloon catheter 410.

Introduction of the optomedical device 10 into the posterior cerebral artery 310 may be accomplished in almost the same way as used for indwelling any known stent in the blood vessel. A typical procedure for introduction is explained below.

First, a guide wire is inserted into the femoral artery of the inguinal region. Next, the guide wire is advanced upward and inserted into the carotid artery, with the help of X-ray radiography to monitor the position of the guide wire. After passing through the carotid artery, the guide wire is introduced into the posterior cerebral artery 310. The inserted guide wire helps the balloon 411 of the balloon catheter 410, which carries the optomedical device 10, to be inserted along it into the posterior cerebral artery 310.

After insertion into the posterior cerebral artery 310, the balloon 411 of the balloon catheter 410 is expanded by means of a pressurized fluid. The expanded balloon 411 expands the main body 20 of the optomedical device 10. Subsequently, the balloon 411 is contracted.

The main body 20 of the optomedical device 10 in its expanded state indwells in the posterior cerebral artery 310. With the balloon 411 contracted, the balloon catheter 410 is withdrawn from the living body. As mentioned above, the optomedical device 10 can be introduced into the cerebral blood vessel 300 in the same way as conventionally employed for the balloon catheter 410, and hence it saves time for operation and burden on the subject.

FIG. 3B is a cross sectional view of the optomedical device 10 indwelling in the posterior cerebral artery 310.

The main body 20 of the optomedical device 10 has the barrel 23 which is hollow, so that blood flowing through the posterior cerebral artery 310 passes through the inside of the main body 20. Thus the indwelling optomedical device 10 does not interfere with the blood flow through the posterior cerebral artery 310.

The optomedical device 10 is constructed such that the light emitting unit 30 is arranged on the outer surface 24 of the main body 20. This construction avoids thrombosis which might occur if the light emitting unit 30 is arranged on the inner surface of the main body 20 and blood flowing through the main body 20 comes into contact with the light emitting unit 30. Moreover, the light emitting unit 30 arranged on the outer surface 24 of the main body 20 remains in contact with the inner wall of the blood vessel while the optomedical device 10 is indwelling in the cerebral blood vessel 300. Consequently, the light (indicated by an arrow F in FIG. 3B) being radiated from the light emitting unit 30 penetrates the wall of the blood vessel and disperses into the brain without being attenuated remarkably.

Finally, the operating device 150 is put on the subject.

The operating device 150 has its current source turned on, so that the detecting unit 156 thereof becomes active. The detecting unit 156 detects the drift eyeball movement of the subject and acquires the sampling value Fs from the amount of drift. The sampling value Fs is used for the determination unit 154 of the operating device 150 to determine the physiological state of the subject, as mentioned above. Depending on the result of determination, the optomedical device 10 activates or deactivates the action of light radiation. If the result of determination is that the sampling value Fs is within the first threshold value F 1, ultraviolet light is radiated to accelerate the release of dopamine.

Detection by the detecting unit 156 and determination by the determination unit 154 may be executed several times over a prescribed period of time according to a proper setting. The timing for light radiation to be activated or deactivated may be set up according to the physiological state of the subject while the optomedical device 10 is indwelling in the cerebral blood vessel 300. Repeated detection and determination may be performed according to the program installed in the control unit 151 of the operating device 150. The time interval for detection by the detecting unit 156 and determination by the determination unit 154 may be set up arbitrarily.

The method for accelerating the release of neurotransmitters by means of the optomedical device 10 should preferably be used in such a way that the light radiating from the inside of the cerebral blood vessel 300 impinges on the pineal body 210 existing in the brain 200. The pineal body 210 has the light receiving function and releases neurotransmitters upon stimulation by light irradiation, as mentioned above. In other words, the release of neurotransmitters is efficiently accelerated by irradiation of the pineal body 210 with light. Incidentally, as shown in FIG. 3B, for the pineal body 210 to be irradiated with light emitted from the light emitting unit 30 of the optomedical device 10, it is desirable to locate the optomedical device 10 such that the light emitting unit 30 faces the pineal body 210.

The foregoing method is intended to radiate ultraviolet light from inside the cerebral blood vessel 300, thereby accelerating the release of dopamine as a neurotransmitter. The method may be modified by replacing the ultraviolet light by blue light, thereby accelerating the release of serotonin, or by radiating ultraviolet light and blue light selectively, thereby accelerating the release of dopamine and serotonin selectively. This modification may be achieved by using the algorithm shown in FIG. 5, for example. According to this algorithm, while ultraviolet light is being radiated, blue light is radiated at an arbitrary timing or when any change in physiological state is detected, so that the release of serotonin is accelerated. The timing for radiation of blue light and the switching between radiation of ultraviolet light and radiation of blue light may be accomplished by the control unit 41 of the optomedical device 10.

The first embodiment mentioned above provides the method for accelerating the release of neurotransmitters. The object of this method is achieved by the step of radiating light into the brain 200 from inside the cerebral blood vessel 300, so that the thus radiated light stimulates the photoreceptor existing within the brain 200, thereby adequately accelerating the release of neurotransmitters. As compared with the conventional method of irradiating the retina with light to accelerate the release of neurotransmitters, the method of the first embodiment offers an advantage of reducing burdens on the human body.

The radiation of light to the pineal body 210 from inside the cerebral blood vessel 300, which is performed in the light emitting step, efficiently accelerates the release of neurotransmitters.

The radiation of light from the posterior cerebral artery 310 and/or the side branch 311 thereof (which are the cerebral blood vessels 300) ensures irradiation of the pineal body 210 with light, thereby efficiently accelerating the release of neurotransmitters.

The radiation of light from the medial posterior choroidal artery 312 (which is one of the side branches 311 of the posterior cerebral artery 310) ensures irradiation of the pineal body 210 with light, thereby more efficiently accelerating the release of neurotransmitters.

The radiation of ultraviolet light (which is performed in the light emitting step) accelerates the release of dopamine as a neurotransmitter. This contributes to the improvement and remedy of various diseases resulting from the insufficient secretion of dopamine or the anomaly of dopamine transmission in the neurotransmission pathway.

The radiation of blue light (which is performed in the light emitting step) accelerates the release of serotonin as a neurotransmitter. This contributes to the improvement and remedy of various diseases resulting from the insufficient secretion of serotonin.

Upon introduction into the cerebral blood vessel 300, the optomedical device 10 provided with the light emitting unit 30 (which radiates light) radiates light through the blood vessel. The light radiation in this manner accelerates the release of neurotransmitters.

The fact that the optomedical device 10 includes the main body 20 of stent type (capable of indwelling in the cerebral blood vessel 300) and the light emitting unit 30 arranged on the outer surface 24 of the main body 20 facilitates the indwelling of the optomedical device 10 in the cerebral blood vessel 300 while preventing hindrance of the blood flow by the light emitting unit 30 and also avoiding the possibility of thrombosis occurring due to the indwelling of the optomedical device 10.

The optomedical device 10 pertaining to this embodiment radiates light from inside the cerebral blood vessel 300, thereby stimulating the photoreceptor existing in the brain 200 and accelerating the release of neurotransmitters. Therefore, it reduces burdens on the subject being treated.

The optomedical device 10, which is constructed such that the main body 20 thereof has the first opening 21, the second opening 22, and the barrel 23, is capable of indwelling without hindrance to blood flow in the cerebral blood vessel 300. This ensures its safety in use as a medical device. Moreover, the ability of the main body 20 to be deformed and expanded in the cerebral blood vessel 300 permits the optomedical device 10 to be placed easily in the blood vessel and to be left there safely for an extended period of time.

The optomedical device 10 is constructed such that the main body 20 thereof has the light emitting unit 30 on the outer surface 24 thereof. The structure prevents the light emitting unit 30 from hindering the blood flow. This facilitates the prevention of thrombosis caused by the indwelling of the optomedical device 10.

Being formed in a cylindrical shape, the main body 20 comes into contact with the inner wall of the cerebral blood vessel 300 over a certain longitudinal length while the optomedical device 10 is left indwelling. This ensures stable indwelling over an extended period of time.

The light emitting unit 30 radiates ultraviolet light and/or blue light so as to accelerate the release of dopamine and serotonin as neurotransmitters.

The optomedical system 100 pertaining to this embodiment is constructed such that the light emitting action by the optomedical device 10 (which has been introduced into the cerebral blood vessel 300) is activated and deactivated by means of the operating device 150 which is placed outside the brain 200. This structure makes the optomedical system easy to operate.

The operating device 150 has the detecting unit 156 that detects the physiological state of the subject, and the result of detection is used to activate and deactivate the action of light radiation. This mechanism permits the process for accelerating the release of neurotransmitters to be performed or suspended at any desirable timing.

Being so constructed as to detect the physiological state of the subject by observing the movement of the subject's eyes, the detecting unit 156 is capable of accurately detecting change in physiological state from varying eye movement.

According to this embodiment, the detection of physiological state is accomplished by comparing the sampling value Fs (which is the amount of drift of the eyeball movement that occurs when the subject views an object) with the first threshold value F1 and the second threshold value F2, both indicating the physiological state. Detection in this manner makes it possible to clearly determine the subject's physiological state to be classified by the eyeball movement.

The optomedical device 10 is controlled intermittently for a certain period of time according to the physiological state detected by the detecting unit 156. This makes it possible to control when to activate and deactivate the action of light radiation depending on the subject's physiological state while the optomedical device 10 is indwelling in the cerebral blood vessel 300.

According to this embodiment, the operating device 150 has the frame 159 (resembling an eyeglass) that can be worn on the subject's ears. Thanks to this structure, the operating device 150 can be made small in size and desirable in appearance.

The Second Embodiment

The following describes the optomedical system pertaining to a second embodiment of the present invention. The optomedical systems pertaining to the first and second embodiments are similar to each other in their structure except for some aspects. The description of their common structure is omitted.

Figure 7:
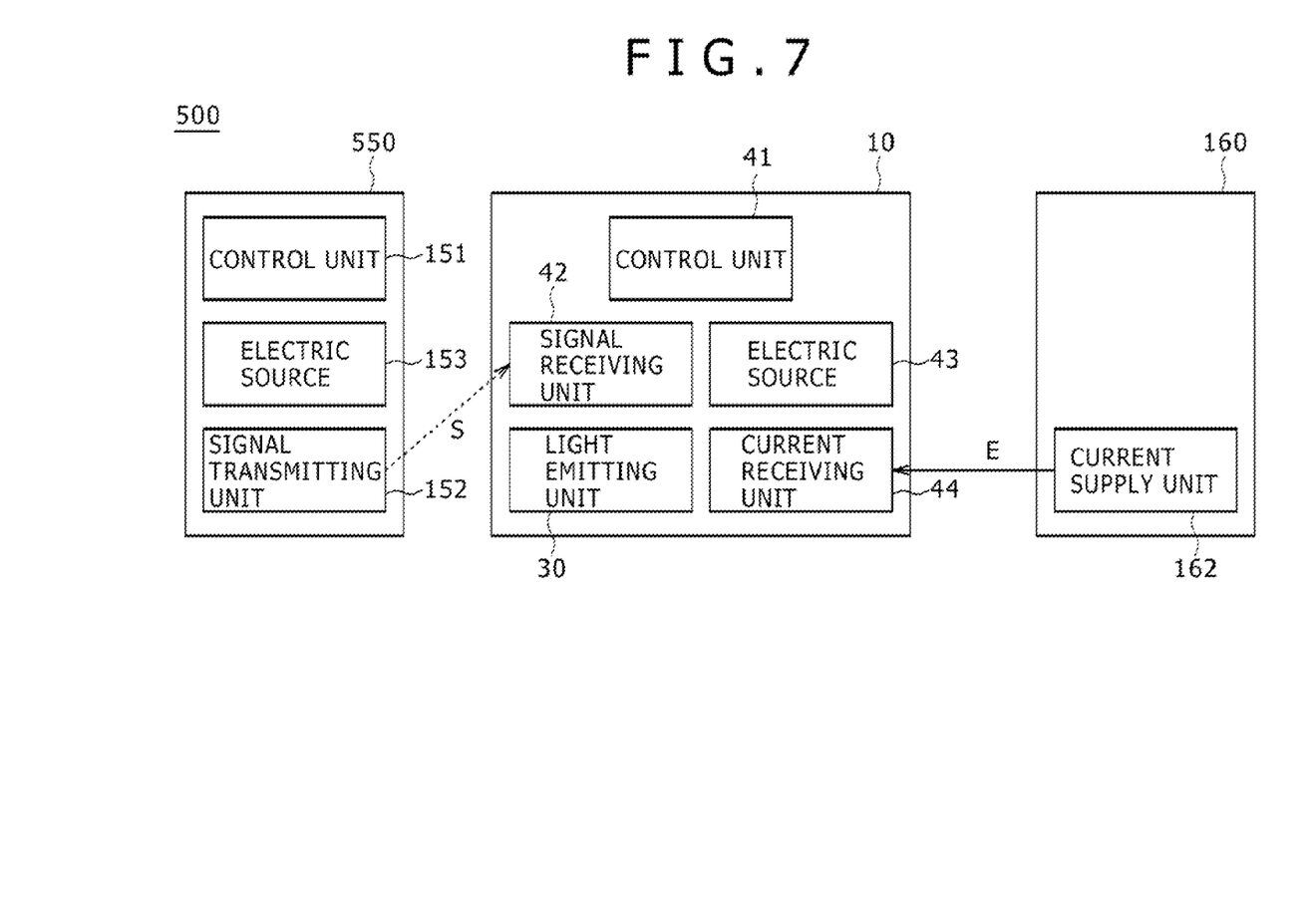
FIG. 7 is a simplified block diagram showing the entire configuration of the optomedical system pertaining to a second embodiment.

The optomedical system 100 according to the first embodiment mentioned above is constructed such that the operating device 150 has the detecting unit 156, which detects the subject's physiological state, and the determination unit 154, which allows the optomedical device 10 to work according to the result of determination, whereas an operating device 550 of an optomedical system 500 pertaining to the second embodiment lacks the detecting unit and the determination unit as shown in FIG. 7. Thus the optomedical system 500 does not detect automatically the subject's physiological state during its operation and hence does not perform action control according to the result of detection. Consequently, the optomedical system 500 needs the subject to directly manipulate the operating device 550 for operation of the optomedical device 10 outside the cerebral blood vessel 300.

The operating device 550 is provided with a switch (not shown) to actuate transmission of control signals to the optomedical device 10. This switch causes the optomedical device 10 to start and suspend the action of light radiation. The operating device 550 may be additionally provided with a switch to change the characteristic properties (such as wavelength, amount of light, and mode of light radiation) of the light radiated from the optomedical device 10. The optomedical device 10 may also be additionally equipped with a timer to control the timing for the action of light radiation to be performed at a prescribed hour and/or for a prescribed period of time.

Although the optomedical system 500 according to this embodiment does not have the function to detect physiological state and the automatic control function that works in response the detected result, the optomedical system 500 causes the optomedical device 10 to radiate light as the operating device 550 is manipulated outside the subject's body. The light radiated in this manner properly accelerates the release of neurotransmitters in the brain.

The Third Embodiment

The following describes the optomedical system pertaining to a third embodiment of the present invention. The optomedical systems pertaining to the first, second, and third embodiments are similar to one another in their structure except for some aspects. The description of their common structure is omitted.

Figure 8:
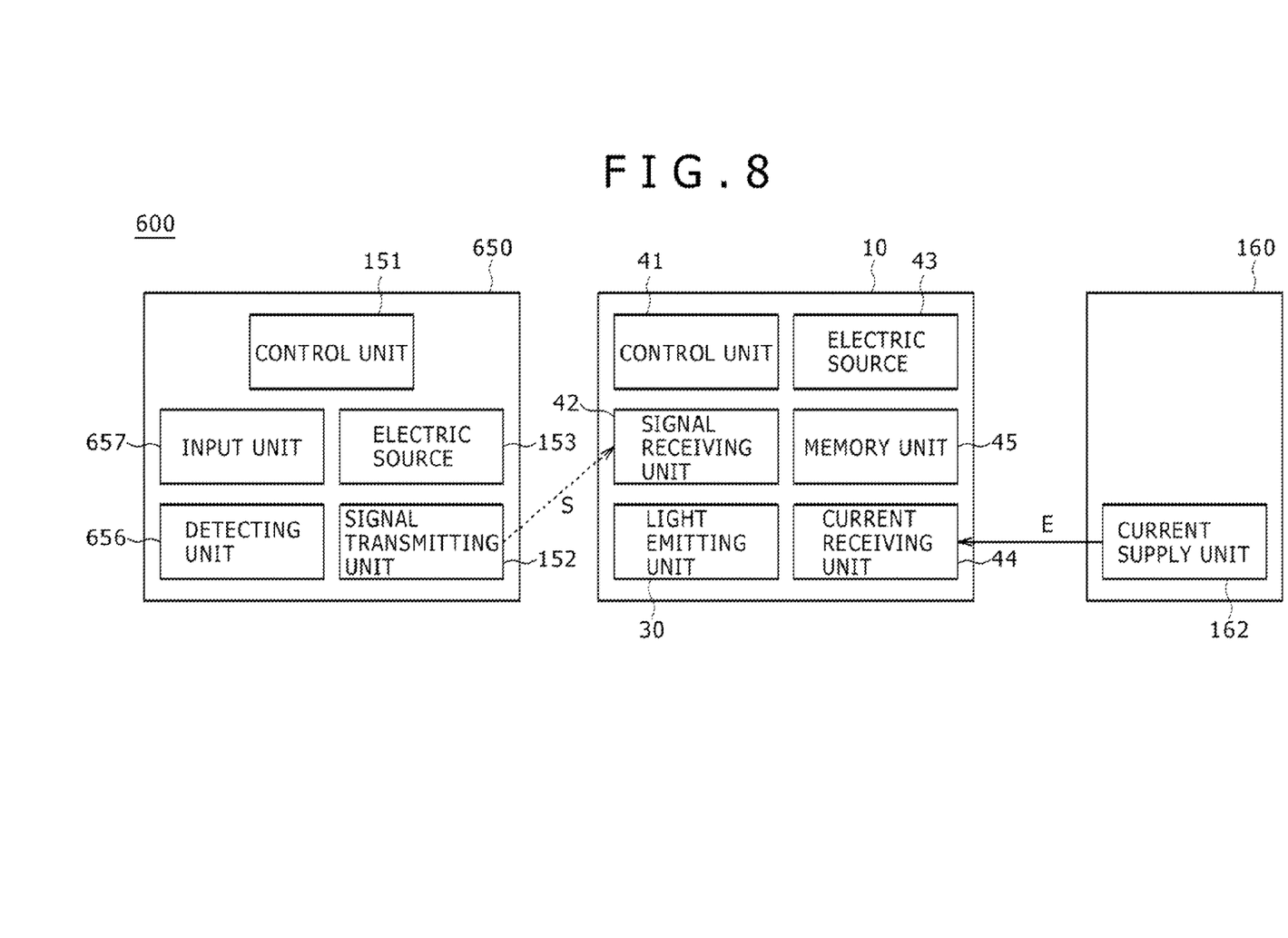
FIG. 8 is a simplified block diagram showing the entire configuration of the optomedical system pertaining to a third embodiment.

As shown in FIG. 8, an optomedical system 600 pertaining to the third embodiment is equipped with an operating device 650 which has a detecting unit 656. The detecting unit 656 detects the sleeping state as one of the physiological states of the subject.

The detecting unit 656 may be any known sensor (such as CMOS sensor and CCD sensor) which is capable of observing the subject's eye movement.

If the detecting unit 656 detects that the subject is keeping his eye closed for a certain period of time, the operating device 650 determines that the subject is sleeping. In response to the result of the determination, the operating device 650 transmits control signals to the optomedical device 10 to control the action thereof. It is possible to set the detecting unit 656 such that it detects the action of the eyelid. For example, if the detecting unit 656 detects that the eyelid remains closed for a period of time longer than a prescribed limit, then the subject is assumed to be sleeping. Incidentally, the optomedical system 600 pertaining to the third embodiment is designed such that a control unit 151 of the operating device 650 functions also as the determination unit if it executes a prescribed program.

The optomedical device 10 may be equipped with a memory unit 45 which stores a program for the timer function to be added to the optomedical device 10. This program allows the light emitting action to be activated and deactivated according to prescribed timing (for example, at a prescribed hour and/or for a prescribed period of time).

The timing may be altered by properly setting the operating device 650 through an input unit 657. Entry of a new value (for timing) into the input unit 657 will change the setting. The input unit 657 may include a touch panel of static capacity type and switches to enter numerical values.

The optomedical system discussed above may be used in the following way.

While the subject is sleeping, the operating device 150 transmits control signals to instruct the optomedical device 10 not to radiate light. When the subject wakes up, the detection unit 656 detects the action of the eyelid, and the control unit 151 determines that the subject is in the state of wakefulness. In response to this determination, the optomedical device 10 causes light (which accelerates the release of neurotransmitters) to be radiated in the cerebral blood vessel 300. The radiated light accelerates the release of neurotransmitters, such as dopamine and serotonin, according to the type of the light. For example, the accelerated release of serotonin resets the subject's internal clock. This makes it easy to control the subject's physical conditions.

The timer function causes the action of light radiation to take place automatically after the elapse of a prescribed period of time. For example, if an ordinary sleeping time is set in the timer, the action of light radiation takes place after the subject has awoken from a sleep. This setting is useful to make the brain active immediately after waking.

As mentioned above, the optomedical system 600 pertaining to the third embodiment works in such a way that control signals to deactivate the action of light radiation is transmitted when the detecting unit 656 detects that the subject is sleeping. The action to suspend the light radiation saves effort to manipulate the optomedical device 10 indwelling in the cerebral blood vessel 300.

Moreover, the optomedical system 600 is construed such that the action of light radiation is activated and deactivated according to the preset time and/or preset time interval. This permits adequate timing control to accelerate the release of neurotransmitters.

Modified Embodiments

The above-mentioned embodiments may be modified in the following manner. For example, the main body of the optomedical device which is formed from an approximately cylindrical stent in the first embodiment may be changed in shape and structure as explained below.

Figure 9A:
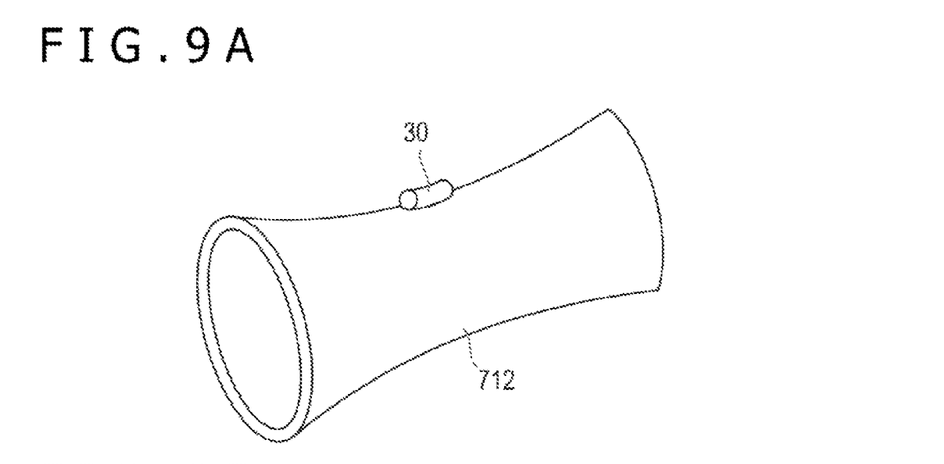
FIGS. 9A, 9B, and 9C are diagrams showing some examples of modifications made to a main body of the optomedical device.

In the case of an optomedical device 710 shown in FIG. 9A as an example of modification, a main body 712 is formed from any member other than stent. Such a member may be made of a known biocompatible material. Moreover, the main body 712 may be expandable or non-expandable. The illustrated example has the openings at its both ends which are larger in outside diameter than the central part. It may also be constructed such that the outside diameter is uniform over the entire length. The central part (barrel) may be hollow so that it does not hinder blood flow.

Figure 9B:
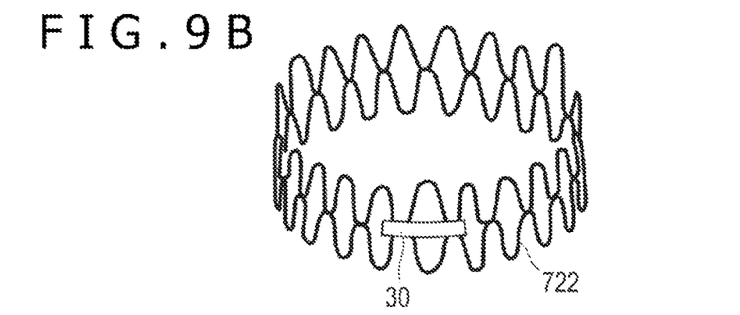

In the case of an optomedical device 720 shown in FIG. 9B as an example of modification, a main body 722 is formed from a ringlike stent. The advantage of the main body 722 of this type is that the external surface area in contact with the inner wall of the blood vessel is smaller than that of the optomedical device 10 explained in the first embodiment. Therefore, the indwelling optomedical device 720 ensures smooth blood flow in the cerebral blood vessel 300.

The main body 722 may be formed from the same material as used for the main body 20 of the optomedical device 10 in the first embodiment. It may also be a stent of self-expandable type or a stent expandable by a balloon catheter.

Figure 9C:
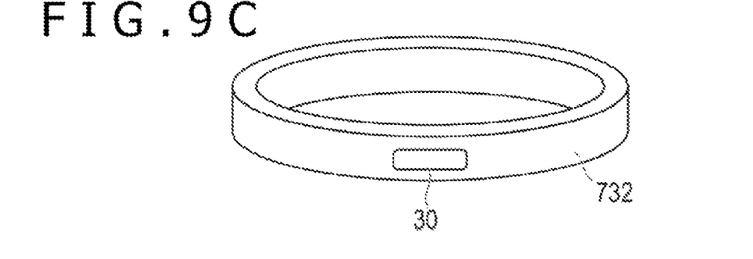

In the case of an optomedical device 730 shown in FIG. 9C as an additional example of modification, a main body 732 is formed from a ringlike member other than stent. The main body 732 of this type too permits the indwelling optomedical device 730 to ensure smooth blood flow in the cerebral blood vessel 300.

In the modified embodiments mentioned above, the main body of the optomedical device may take any shape and structure so long as it can be introduced into the cerebral blood vessel. Therefore, it may be modified in any way to facilitate its introduction into the cerebral blood vessel and ensure its easy use.

The above-mentioned embodiments and modifications thereof have demonstrated certain embodiments of the present invention which cover the method for accelerating the release of neurotransmitters, the optomedical device, and the optomedical system. They may be changed and modified as shown below.

The method for accelerating the release of neurotransmitters may be modified such that the optomedical device is not placed (for indwelling) in the cerebral blood vessel. It is possible to accelerate the release of neurotransmitters even though the following steps are employed. That is, a device capable of light radiation is placed in the cerebral blood vessel, the device is allowed to radiate light, and finally the device is taken out of the cerebral blood vessel.

The light suitable for radiation in the cerebral blood vessel is not restricted to ultraviolet light and blue light. Any light varying in wavelength can be used depending on the kind of the neurotransmitters to be released at an accelerated rate. Moreover, the neurotransmitters to be released at an accelerated rate are not restricted to dopamine and serotonin; they include any species which are released at an accelerated rate by the light radiated from inside the cerebral blood vessel.

The optomedical device can also be used alone without the help of the operating device and the current supply device. In the case where the current supply device is omitted, the optomedical device may be equipped with the current supply unit such as battery and cell.

The detecting unit may be constructed in any way so long as it is capable of detecting the subject's physiological state. In other words, it may be so constructed as to detect any physiological phenomena other than the eyeball movement and the opening and closing of the eyelid. Therefore, the devices and systems mentioned above may be so constructed as to detect the respiration rate, the pulse, and the surface muscular motion of the face, thereby determining the subject's physiological state.

It should be understood by those skilled in the art that various modifications, combinations, sub-combinations and alterations may occur depending on design requirements and other factors insofar as they are within the scope of the appended claims or the equivalents thereof.

What is claimed is:

1. A method for accelerating the release of neurotransmitters, the method comprising:
    radiating light from within a posterior cerebral artery and/or a direct branch thereof to accelerate the release of the neurotransmitters,
    wherein the light radiated from within the posterior cerebral artery and/or the direct branch thereof is directed to a pineal body.

2. The method according to claim 1, wherein the light radiated from within the posterior cerebral artery and/or the direct branch thereof is ultraviolet light.

3. The method according to claim 1, wherein the light radiated from within the posterior cerebral artery and/or the direct branch thereof is blue light.

4. The method according to claim 1, further comprising introducing into the posterior cerebral artery and/or the direct branch thereof an optomedical device having a light emitting unit configured to radiate the light.

5. The method according to claim 4, wherein the optomedical device comprises:
    a stent capable of indwelling in the posterior cerebral artery and/or the direct branch thereof; and
    the light emitting unit arranged on the outer surface of the stent.

6. A method for accelerating the release of neurotransmitters, the method comprising:
    radiating light from within a medial posterior choroidal artery to accelerate the release of the neurotransmitters,
    wherein the light radiated from within the medial posterior choroidal artery is directed to a pineal body.

7. The method according to claim 6, wherein the light radiated from within the medial posterior choroidal artery is ultraviolet light.

8. The method according to claim 6, wherein the light radiated from within the medial posterior choroidal artery is blue light.

9. The method according to claim 6, further comprising introducing into the medial posterior choroidal artery an optomedical device having a light emitting unit configured to radiate the light.

10. The method according to claim 9, wherein the optomedical device comprises:
    a stent capable of indwelling in the medial posterior choroidal artery; and
    the light emitting unit arranged on the outer surface of the stent.

11. A method for accelerating the release of neurotransmitters, the method comprising:
    introducing into a cerebral blood vessel an optomedical device having a light emitting unit configured to radiate light, wherein the optomedical device comprises a stent capable of indwelling in the cerebral blood vessel, and a light emitting unit arranged on the outer surface of the stent, the light emitting unit being configured to radiate light;
    using the light emitting unit of the optomedical device to radiate light from within the cerebral blood vessel to accelerate the release of the neurotransmitters.

12. The method according to claim 11, wherein the light radiated from within the cerebral blood vessel is directed to a pineal body.

13. The method according to claim 11, wherein the cerebral blood vessel is a posterior cerebral artery and/or a direct branch thereof.

14. The method according to claim 11, wherein the cerebral blood vessel is a medial posterior choroidal artery.

15. The method according to claim 11, wherein the light radiated from within the cerebral blood vessel is ultraviolet light.

16. The method according to claim 11, wherein the light radiated from within the cerebral blood vessel is blue light.

* * * * *